(12) United States Patent
Pai et al.

(10) Patent No.: US 11,523,931 B2
(45) Date of Patent: Dec. 13, 2022

(54) SYSTEMS AND METHODS FOR PROVIDING PENILE MODELING

(71) Applicant: Lamamed Solutions, Inc., Hayward, CA (US)

(72) Inventors: Suresh Subraya Pai, Los Altos, CA (US); Celso Jacinto Bagaoisan, Union City, CA (US); Ian L. Goldman, Scottsdale, AZ (US); John M Strobel, Solon, OH (US)

( * ) Notice: Subject to any disclaimer, the term of this patent is extended or adjusted under 35 U.S.C. 154(b) by 0 days.

(21) Appl. No.: 17/289,890

(22) PCT Filed: Nov. 11, 2019

(86) PCT No.: PCT/US2019/060805
§ 371 (c)(1),
(2) Date: Apr. 29, 2021

(87) PCT Pub. No.: WO2020/102120
PCT Pub. Date: May 22, 2020

(65) Prior Publication Data
US 2021/0401611 A1 Dec. 30, 2021

Related U.S. Application Data

(60) Provisional application No. 62/768,316, filed on Nov. 16, 2018.

(51) Int. Cl.
*A61F 5/41* (2006.01)
(52) U.S. Cl.
CPC .......... *A61F 5/41* (2013.01); *A61F 2005/414* (2013.01); *A61F 2005/415* (2013.01)

(58) Field of Classification Search
CPC ........ A61F 2/26; A61F 5/41; A61F 2005/414; A61F 2005/415
See application file for complete search history.

(56) References Cited

U.S. PATENT DOCUMENTS

| | | | | |
|---|---|---|---|---|
| 5,360,390 A | * | 11/1994 | Maanum | A61F 5/41 600/39 |
| 5,730,154 A | * | 3/1998 | DeRidder | A61F 5/05841 128/880 |
| 5,997,470 A | * | 12/1999 | Coates | A61F 5/41 600/41 |
| 6,015,379 A | * | 1/2000 | Sachse | A61F 5/41 600/38 |
| 6,277,063 B1 | * | 8/2001 | Altshuler | A61F 5/41 600/39 |

(Continued)

*Primary Examiner* — Samuel G Gilbert
(74) *Attorney, Agent, or Firm* — Jonathan D Feuchtwang

(57) ABSTRACT

A device for remodeling a penis, comprising a generally cylindrical hollow assembly having a lumen extending between proximal and distal ends, the distal end being in communication with the lumen to facilitate insertion of the penis into the lumen, the generally cylindrical structure having an interior surface facing the lumen and an exterior surface facing away from the lumen, a longitudinal direction and a transverse direction, the transverse direction being orthogonal to the longitudinal direction, the generally cylindrical assembly adapted to snugly and resiliently grip the penis, and includes an elastic fabric with one or more regions reinforced with a plastically deformable member.

13 Claims, 12 Drawing Sheets

(56) References Cited

U.S. PATENT DOCUMENTS

| | | | | |
|---|---|---|---|---|
| 8,585,753 B2* | 11/2013 | Scanlon | ................ | B29C 55/26 |
| | | | | 623/1.42 |
| 2007/0068965 A1* | 3/2007 | Von Flotow | ....... | B65D 75/5805 |
| | | | | 383/905 |
| 2012/0136206 A1* | 5/2012 | Deitch | ..................... | A61F 5/41 |
| | | | | 600/39 |
| 2014/0135574 A1* | 5/2014 | Gannam | ............... | A61H 19/32 |
| | | | | 600/38 |
| 2015/0094528 A1* | 4/2015 | Deitch | ..................... | A61F 2/26 |
| | | | | 600/40 |

* cited by examiner

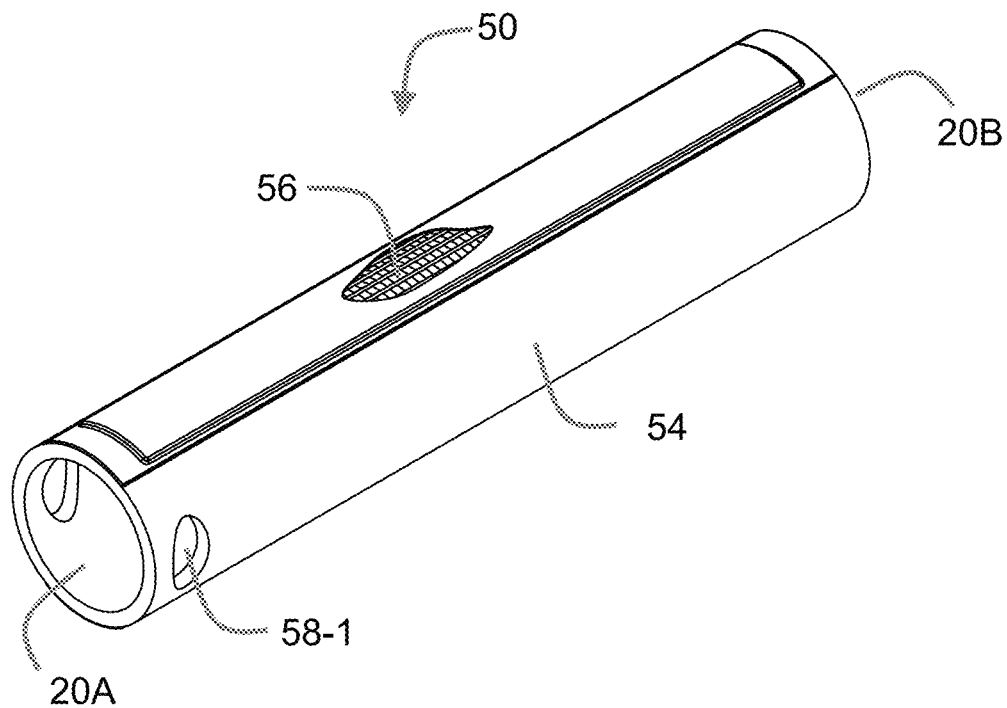
Figure 5C-1
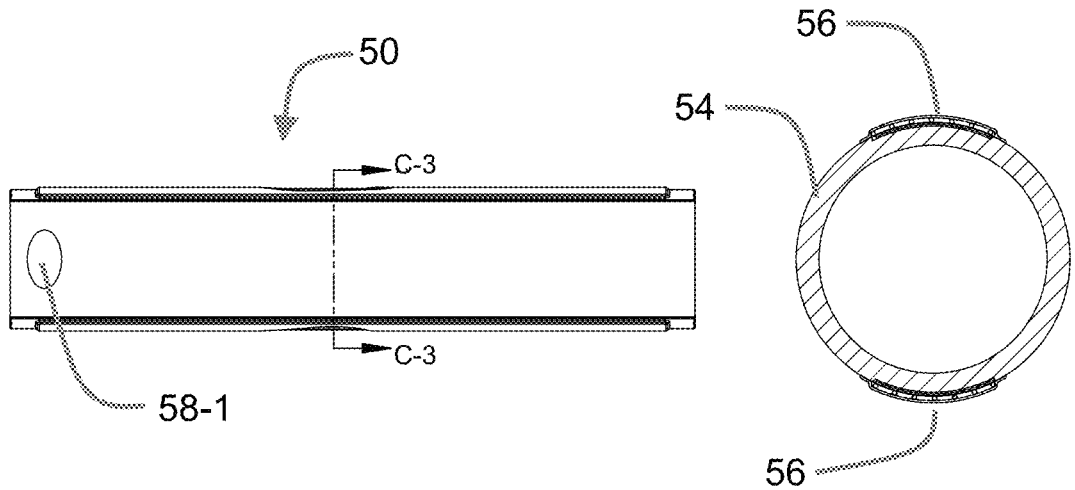
Figure 5C-2
Figure 5C-3

SYSTEMS AND METHODS FOR PROVIDING PENILE MODELING

BACKGROUND

Peyronie's disease is a connective tissue disorder. It involves the unwanted growth of fibrous plaques in the soft tissue of the penis. Specifically, in those affected, scar tissue forms in the tunica albuginea, the thick sheath of tissue surrounding the corpora cavernosa. This can cause abnormal and undesirable curvature of the penis, pain, erectile dysfunction, and other undesirable side effects.

Treatments for erectile dysfunction have advanced in recent years, and include both medical and surgical remediation approaches. In one surgical treatment approach to erectile dysfunction, inflatable implants are placed within the penis, along with a pump and fluid reservoir that are also implanted in other areas of the patient's body. After healing, the patient may then be able to achieve erection when the pump is actuated to transfer fluid into the inflatable implants, and to terminate the artificial erection through release of the fluid back into the fluid reservoir. At the time of implantation, surgeons may also perform penile modeling to achieve optimum placement of the penile implants in persons affected by Peyronie's disease, more specifically, in patients having a penis with a noticeable curvature. However, such modeling requires the surgeon to inflate the penile implants, and apply counteracting physical force for a prolonged period to achieve a desired amount of straightening to Peyronie's-affected patients. This process is time consuming and can be uncomfortable for the surgeon to perform. Further, holding the desired position for extended periods may cause significant fatigue and even pain on the part of the surgeon and may lead to less than desired remodeling results of the surgically-altered penis. In addition, patients are encouraged to continue penile remodeling using the device at home after surgery or other treatment for Peyronie's disease.

It is therefore desirable to provide improved systems and methods to assist surgeons and patients with reduction of undesirable penile curvature resulting from Peyronie's disease.

SUMMARY OF THE INVENTION

A first example device for remodeling a penis, comprising: a generally cylindrical hollow assembly having a lumen extending between proximal and distal ends, the distal end being in communication with the lumen to facilitate insertion of the penis into the lumen, the generally cylindrical structure having an interior surface facing the lumen and an exterior surface facing away from the lumen, a longitudinal direction and a transverse direction, the transverse direction being orthogonal to the longitudinal direction, the generally cylindrical assembly adapted to snugly and resiliently grip the penis, and includes an elastic fabric with one or more regions reinforced with a plastically deformable member.

The first example device, wherein the proximal end of the assembly is in communication with the lumen and is sized to accommodate the hub of a delivery catheter.

The first example device, wherein the plastically deformable member is solid.

The first example device, wherein the plastically deformable member is a mesh.

The first example device, wherein the plastically deformable member is at least partially coated by a coating, covered by the elastic fabric, or embedded within the elastic fabric.

The first example device, wherein the elastic fabric is elected from the group (Neoprene, Lycra, Spandex, silicone rubber, polyurethane, latex, vulcanized rubber, thermoplastic elastomers, polypropylene, ePTFE, Teflon, non-woven fabrics, woven fabrics, knit fabrics).

The first example device, comprising at least one through-hole extending through a wall of the cylindrical assembly.

The first example device, wherein the plastically deformable member is formed of a material selected from the group (aluminum, steel, non-hardened soft steel alloys, plastic, polymeric materials, polypropylene, nylon, polyethylene, polycarbonate, and urethanes).

The first example device, wherein the proximal and distal ends are atraumatic.

The first example device, wherein the plastically deformable member is malleable at room temperature.

The first example device, wherein the proximal and distal ends are covered with an atraumatic material.

The first example device, further comprising at least one inflatable lining provided on the interior surface, each one of the at least one inflatable lining being independently inflatable, thereby providing one or more inflatable regions.

A delivery device for delivering the remodeling device of the first example device, comprising: a hollow tube having a lumen, the hollow tube having an interior diameter configured to fit over a penis, an exterior diameter configured to coaxially receive the remodeling device, a total length measured between proximal and distal ends of the tube, working length measured between the distal end and a location coincident with or proximal the proximal end and which is less than or equal to the total length.

The delivery device of the preceding example, wherein the exterior diameter is constant over the working length.

The delivery device of any of the preceding examples, further comprising at least one grasping member used to position the delivery device.

The delivery device of any of the preceding examples, wherein the total length is greater than the working length, and the exterior diameter tapers wider from the proximal end to the working length or the exterior diameter tapers wider from the distal end to the working length.

BRIEF DESCRIPTION OF THE DRAWINGS

FIGS. 5A-1 through 5C-3 are views of a fourth exemplary remodeling device;

FIGS. 6A-6C-2 show a delivery device for delivering a remodeling device;

DETAILED DESCRIPTION

Figure 1A:
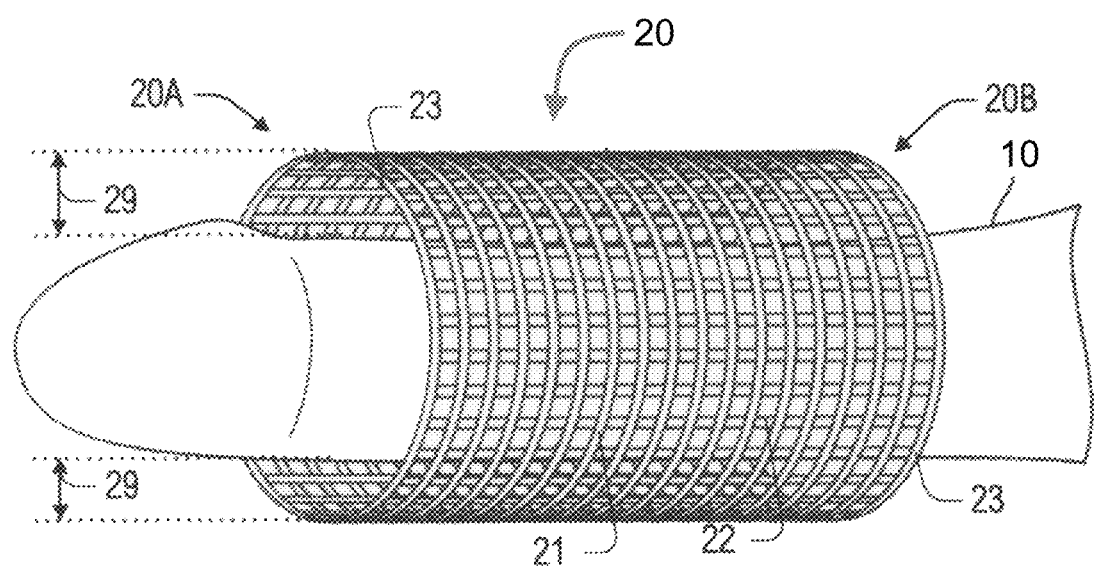
FIGS. 1A-1C are views of a first exemplary remodeling device.
Figure 1B:
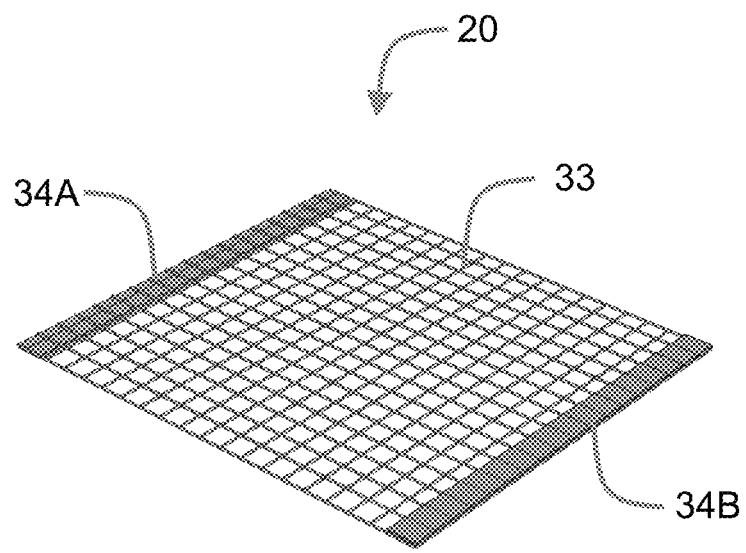

FIGS. 1A and 1B show an exemplary embodiment of a system, consistent with systems and methods of the present invention. A partial view of a patient's penis 10 is shown. The patient is afflicted with Peyronie's disease or any other condition that creates an undesired curvature or bending of the patient's penis. As shown in FIG. 1A, the penis 10 is in a corrected condition (i.e., un-curved); however, those skilled in the art understand that there would be undesired curvature of a penis of a patient suffering from Peyronie's disease.

Also shown in FIG. 1A is a device 20 for penile modeling. Device 20, as shown, includes a generally cylindrical structure or assembly (although any other desired structural shape is permitted), including open ends 20A, 20B to facilitate insertion of device 20, 24, 25, 26, 50, or 70 over penis 10. In any of the examples disclosed herein, end 20A may be sized to accommodate the hub of a standard catheter. For example, if the patient's penis is catheterized, it will be desirable to be able to slide the remodeling device over the catheter without having to remove the catheter and reinstall. The hub of the catheter is typically the widest portion of the catheter, and if the end 20A is able to accommodate the catheter hub then the remodeling device can be slid over the hub to the penis.

Figure 1C:
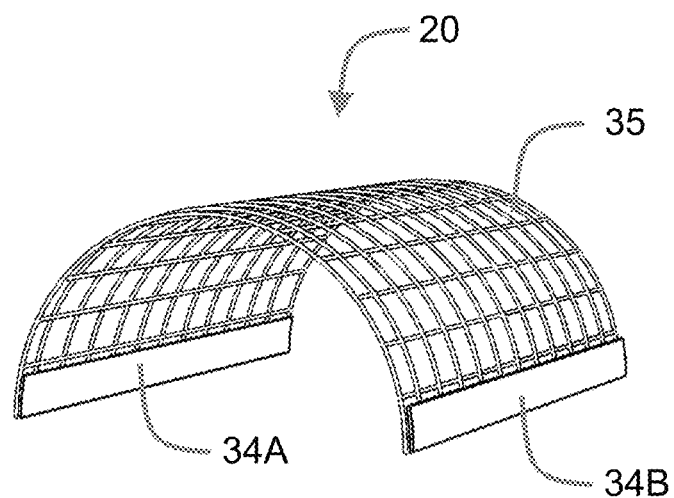

In this embodiment of device 20, an array of orthogonally-arranged structural (malleable or plastically deformable) members 21, 22 creates the structure (assembly) of device 20, including ring closures 23 on the ends of device 20, so that no open-ended structural members 21, 22 are exposed to potentially cause unintended injury to the patient. The space 29 between penis 10 and device 20 is shown expanded for simplification of the drawing; however, in practice, the space 29 between penis 10 and device 20 would be smaller. A variety of diameters of device 20 may be provided to accommodate different anatomical diameters of patients' penises. Alternatively, device 20 may comprise a flat sheet or semi rolled flat sheet of material which is wrapped around the penis 10 to form a cylinder as shown in FIGS. 1B and 1C respectively. The opposed edges of the flat sheet or semi rolled flat sheet may be secured together using conventional closure mechanisms such as a hook-and-loop material (e.g., Velcro®), adhesive tape, clasps or the like (not shown).

The material or materials employed to form the structural (malleable or plastically deformable) members 21, 22 of device 20 may be selected from any desired material or materials, including, without limitation, aluminum, steel and non-hardened soft steel alloys, stainless steel and the like. The desired material or materials forming the structural members 21, 22 of device 20 may establish a rigid structure with a level of malleability (plastically deformable) permitting a caregiver or patient to selectively bend and configure device 20 into a desired shape (i.e., bending device 20 into a "Modeling Configuration") at room temperature. In some examples, the structural members 21, 22 are sufficiently robust to withstand multiple bending and straightening cycles without cracking Specifically, once device 20 is bent into the Modeling Configuration, device 20 retains sufficient structural rigidity to apply a counteracting force against a region of the penis 10 having the undesired curvature, without bending device 20 in a manner that reduces such counteracting force. In other words, the structural rigidity of device 20 is sufficient to prevent the region of undesired penile curvature from changing the shape of the Modeling Configuration.

The structural members of device 20 may also have a coating, covering of material or an elastic fabric or elastomeric sheet covering suitable for the patient's comfort. The coating material, elastic fabric or elastomeric sheeting (not shown) may be provided on the interior surface area of device 20 (i.e., that portion in contact with penis 10), or alternatively, may cover all exposed surfaces of the structural members 21, 22 forming device 20. Exemplary coating materials may include any polymer including, without limitation Neoprene, Lycra, Spandex, silicone rubber, polyurethane, latex, vulcanized rubber, thermoplastic elastomers such as C Flex, polypropylene, ePTFE, Teflon, non-woven, woven or knit fabrics composed of Lycra, cotton or the like, or any other desired material having some flexibility once applied to the structural members 21, 22 forming device 20 and providing some degree of coating compressibility to reduce patient discomfort from application of device 20 in the Modeling Configuration against the penis 10.

In use, device 20 is inserted over or wrapped around the patient's penis 10, as shown in FIG. 1A. The caregiver or patient would then bend device 20 into a shape (i.e., again, "the Modeling Configuration") in which a force would be applied against that portion of the penis 10 having undesired curvature, such that the applied force would tend to straighten out and correct the shape of penis 10. In an alternate approach, during the Modeling Configuration, the surgeon, after installing penile implants, may cause an artificial erection by inflating penile implants, and adjust the shape of the device 20 to counter any undesired bends of the surgically-modified penis that become more apparent upon the artificial erection of the patient's penis. Alternatively, the surgeon may inflate the penile implants after insertion and shape adjustment of the device 20, and iterative inflations and adjustments to the shape of device 20 may be undertaken to achieve the desired straightening effects.

Figure 2:
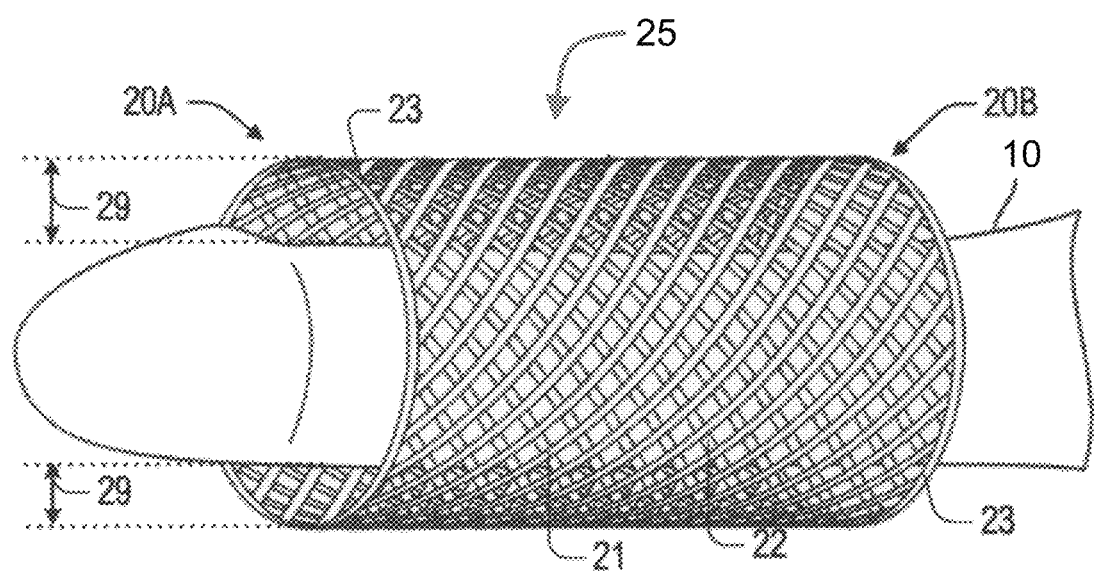
FIG. 2 is an exemplary remodeling device.

FIG. 2 shows another exemplary embodiment of a system, consistent with systems and methods of the present invention. Again, a partial view of a patient's penis 10 is shown, and the patient is afflicted with Peyronie's disease or any other condition that creates an undesired curvature or bending of the patient's penis. Again, as shown in FIG. 2, the penis 10 is in a corrected condition (i.e., un-curved); however, those skilled in the art understand that there would be undesired curvature of a penis of a patient suffering from Peyronie's disease.

Also shown in FIG. 2 is a device 25 for penile modeling. Device 25, as shown, includes a generally cylindrical structure or assembly (although any other desired structural shape is permitted), including open ends 20A, 20B to facilitate insertion of device 25 over penis 10. In this embodiment of device 25, an array of diagonally-arranged structural members 21, 22 creates the structure or assembly of device 25, including ring closures 23 on the ends of device 25, so that no open-ended structural members are exposed to injure the patient. The space 29 between penis 10 and device 25 is expanded for simplification of the drawing; however, in practice, the space 29 between penis 10 and device 25 would be smaller. A variety of diameters of device 25 may be provided to accommodate different anatomical diameters of patients' penises. Alternatively (not shown), device 25 may comprise a flat sheet or semi rolled flat sheet of material which is wrapped around the penis 10 to form a cylinder. The opposed edges of the sheet may be secured together using conventional closure mechanisms such as a hook-and-loop material (e.g., Velcro®), adhesive tape, clasps or the like (not shown).

The material or materials employed to form the structural members 21, 22 of device 25 may be selected from any desired material or materials, including, without limitation, aluminum, steel, and non-hardened soft steel alloys. The desired material or materials forming the structural members 21, 22 of device 25 may establish a rigid structure with a level of malleability (plastic deformability) permitting a caregiver or patient to selectively bend and configure device 25 into a desired shape (i.e., bending device 25 into the Modeling Configuration). Specifically, once device 25 is bent into the Modeling Configuration, device 25 retains sufficient structural rigidity to apply a counteracting force against a region of the penis 10 having the undesired curvature, without bending device 25 in a manner that reduces such counteracting force. In other words, the structural rigidity of device 25 is sufficient to prevent the region of undesired penile curvature from changing the shape of the Modeling Configuration.

The structural members 21, 22 of device 25 may also have a coating of material or include an elastic fabric or elastomeric sheeting suitable for the patient's comfort. The coating material, elastic fabric or elastomeric sheeting (not shown) may reside on only the interior surface area of device 25 (i.e., that portion in contact with penis 10), or alternatively, may cover all exposed surfaces of the structural members 21, 22 forming device 25. Exemplary coating materials including, without limitation Neoprene, Lycra, Spandex, silicone rubber, polyurethane, latex, vulcanized rubber, thermoplastic elastomers such as C Flex®, polypropylene, ePTFE, Teflon, non-woven, woven or knit fabrics composed of Lycra, cotton or the like or any other desired material having some flexibility once applied to the structural members 21, 22 forming device 25 and providing some degree of coating compressibility to reduce patient discomfort from application of device 25 in the Modeling Configuration against the penis 10.

In use, device 25 is inserted over or wrapped around the patient's penis 10, as shown in FIG. 2. The caregiver or patient would then bend device 25 into a shape (i.e., again, the Modeling Configuration) in which a force would be applied against that portion of the penis 10 having undesired curvature, such that the applied force would tend to straighten out and correct the shape of penis 10. In an alternate approach, during the Modeling Configuration, the surgeon, after installing penile implants, may cause an artificial erection by inflating penile implants, and adjust the shape of the device 25 to counter any undesired bends of the surgically-modified penis that become more apparent upon the artificial erection of the patient's penis. Alternatively, the surgeon may inflate the penile implants after insertion and shape adjustment of the device 25, and iterative inflations and adjustments to the shape of device 25 may be undertaken to achieve the desired straightening effects.

Figure 3:
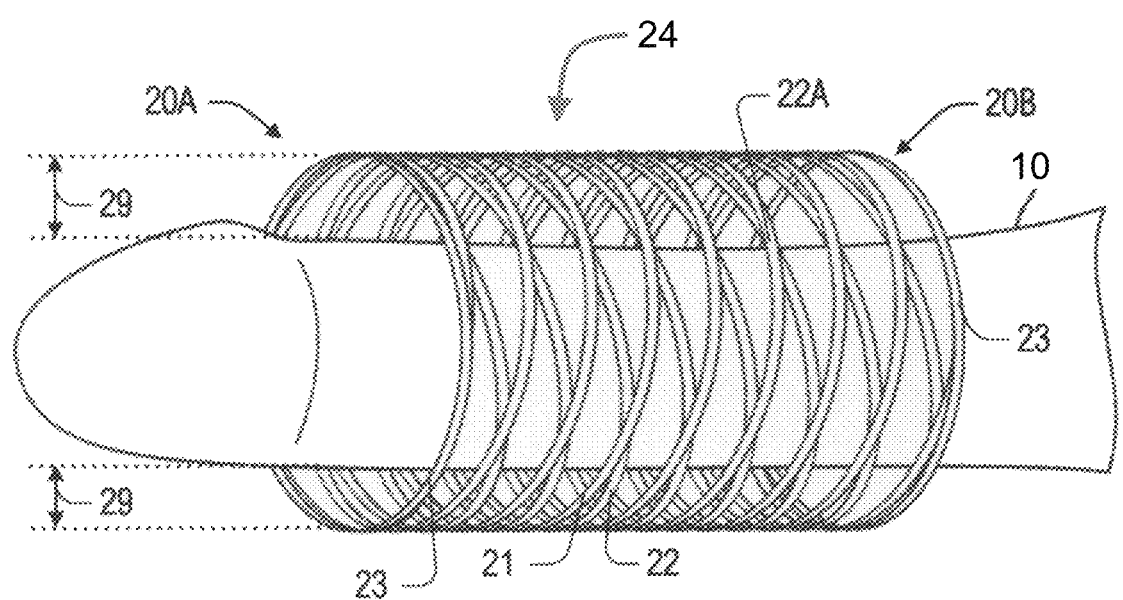
FIG. 3 is a second exemplary remodeling device.

FIG. 3 shows yet another exemplary embodiment of a system, consistent with systems and methods of the present invention. Again, a partial view of a patient's penis 10 is shown, and the patient is afflicted with Peyronie's disease or any other condition that creates an undesired curvature or bending of the patient's penis. Again, as shown in FIG. 3, the penis 10 is in a corrected condition (i.e., un-curved); however, those skilled in the art understand that there would be undesired curvature of a penis of a patient suffering from Peyronie's disease.

Also shown in FIG. 3 is a device 24 for penile modeling. Device 24, as shown, includes a generally cylindrical structure (although any other desired structural shape is permitted), including open ends 20A, 20B to facilitate insertion of device 24 over penis 10. In this embodiment of device 24, two or more opposing helical structures create the structure of device 24. The space 29 between penis 10 and device 24 is expanded for simplification of the drawing; however, in practice, the space 29 between penis 10 and device 24 would be smaller. A variety of diameters of device 24 may be provided to accommodate different anatomical diameters of patients' penises. Alternatively (not shown), device 24 may comprise a flat sheet or semi rolled flat sheet of material which is wrapped around the penis 10 to form a cylinder. The opposed edges of the sheet may be secured together using conventional closure mechanisms such as a hook-and-loop material (e.g., Velcro®), adhesive tape, clasps or the like (not shown).

The material or materials employed to form the structural members 21, 22 of device 24 may be selected from any desired material or materials, including, without limitation, aluminum, steel and non-hardened soft steel alloys. The desired material or materials forming the structural members 21, 22 of device 24 may establish a rigid structure with a level of malleability permitting a caregiver or patient to selectively bend and configure device 24 into a desired shape (i.e., bending device 24 into the Modeling Configuration) at room temperature. In some examples, the structural members 21, 22 are sufficiently robust to withstand multiple bending and straightening cycles without cracking. In one embodiment, at points (such as the location shown in 22A) where structural members 21, 22 approximate contact, structural members 21, 22 may be affixed to one another through application of an adhesive between structural members 21, 22, by enrobement of the device 24 in a polymer or other flexible coating of desired durometer, or by spot welding or brazing at each contact point (such as point 22A). Specifically, once device 24 is bent into the Modeling Configuration, device 24 retains sufficient structural rigidity to apply a counteracting force against a region of the penis 10 having the undesired curvature, without bending device 24 in a manner that reduces such counteracting force. In other words, the structural rigidity of device 24 is sufficient to prevent the region of undesired penile curvature from changing the shape of the Modeling Configuration.

The structural members 21, 22 of device 24 may also have a coating of material or include an elastic fabric or silicone sheeting suitable for the patient's comfort. The coating material, elastic fabric or silicone sheeting (not illustrated) may reside on only the interior surface area of device 24 (i.e., that portion in contact with penis 10), or alternatively, may cover all exposed surfaces of the structural members 21, 22 forming device 24. Exemplary coating materials may including, without limitation Neoprene, Lycra, Spandex, silicone rubber, polyurethane, latex, vulcanized rubber, thermoplastic elastomers such as C Flex®, polypropylene, ePTFE, Teflon, non-woven, woven or knit fabrics composed of Lycra, cotton or the like or any other desired material having some flexibility once applied to the structural members 21, 22 forming device 24 and providing some degree of coating compressibility to reduce patient discomfort from application of device 24 in the Modeling Configuration against the penis 10. Alternatively, the device 24 may be enrobed in a flexible substance such as Neoprene, Lycra, Spandex, silicone rubber, polyurethane, latex, vulcanized rubber, C Flex, polypropylene, ePTFE, Teflon, non-woven, woven or knit fabrics composed of Lycra, cotton or the like or any other material that provides both structural adhesion between structural members 21, 22 and comfort padding for the patient.

In use, device 24 is inserted over or wrapped around the patient's penis 10, as shown in FIG. 3. In examples, in which the device is wrapped around the penis, a delivery device such as shown in FIGS. 6A, 6B, 6C-1 is optional. The caregiver or patient would then bend device 24 into a shape (i.e., again, the Modeling Configuration) in which a force would be applied against that portion of the penis 10 having undesired curvature, such that the applied force would tend to straighten out and correct the shape of penis 10. In an alternate approach, during the Modeling Configuration, the surgeon, after installing penile implants, may cause an artificial erection by inflating penile implants, and adjust the shape of the device 24 to counter any undesired bends of the surgically-modified penis that become more apparent upon the artificial erection of the patient's penis. Alternatively, the surgeon may inflate the penile implants after insertion and shape adjustment of the device 24, and iterative inflations and adjustments to the shape of device 24 may be undertaken to achieve the desired straightening effects.

Figure 4:
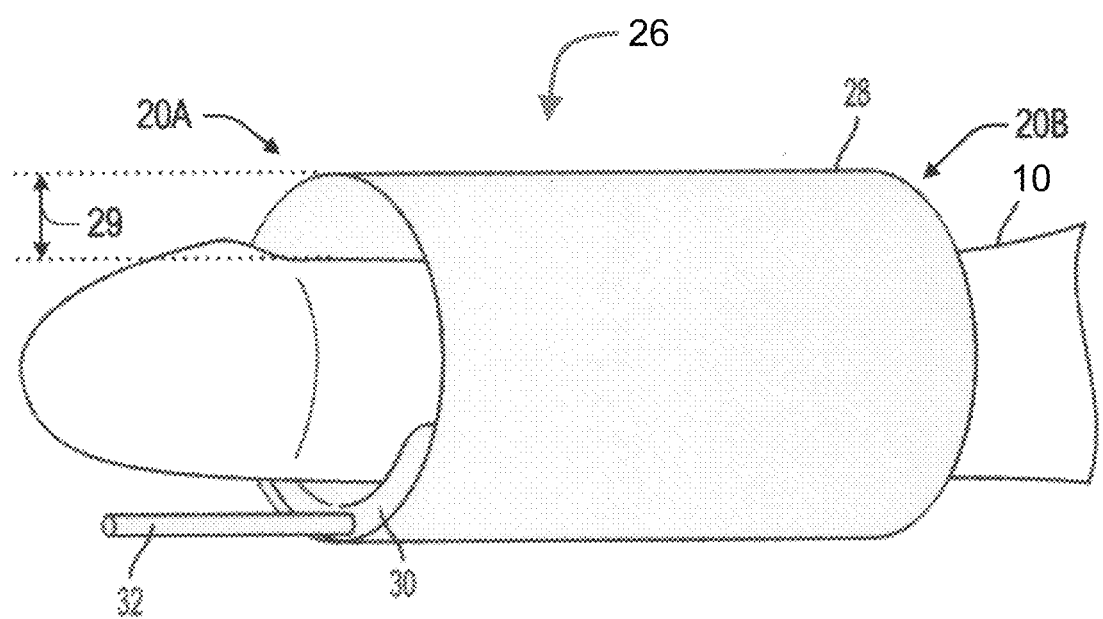
FIG. 4 is a third exemplary remodeling device with an inflatable lining.

FIG. 4 shows still another exemplary embodiment of a system, consistent with systems and methods of the present invention. Again, a partial view of a patient's penis 10 is shown, and the patient is afflicted with Peyronie's disease or any other condition that creates an undesired curvature or bending of the patient's penis. Again, as shown in FIG. 4 the penis 10 is in a corrected condition (i.e., un-curved); however, those skilled in the art understand that there would be undesired curvature of a penis of a patient suffering from Peyronie's disease.

Also shown in FIG. 4 is a device 26 for penile modeling. Device 26 may include a cuff 28, an inflatable lining 30, a tube 32 and a fluid reservoir and pump (not shown) coupled to tube 32.

Device 26, as shown, includes a generally cylindrical structure 28 (although any other desired structural shape is permitted), including open ends 20A, 20B to facilitate insertion of device 26 over penis 10. In this embodiment of device 26, unlike the devices 20-24 that include structural members 21, 22 having openings there-between and forming the overall structure, device 26 provides a rigid or semi-rigid approximately cylindrical sleeve 28. Sleeve 28 may comprise a unitary cylindrical structure, as opposed to a cylindrical structure formed by structural members 21, 22 and having related openings there-between. Alternatively (not shown), sleeve 28 may comprise a sheet of flat material or semi rolled flat material which is wrapped around the penis 10 to form the cylindrical structure. The opposed edges of the sheet may be secured together using conventional closure mechanisms such as a hook-and-loop material (e.g., Velcro®), adhesive tape, clasps or the like (not shown). The space 29 between penis 10 and sleeve 28 is expanded for simplification of the drawing; however, in practice, the space 29 between penis 10 and sleeve 28 would be smaller. A variety of diameters of device 26 may be provided to accommodate different anatomical diameters of patients' penises.

The material or materials employed to form sleeve 28 may be selected from any desired material or materials, including, without limitation, stainless steel and polymers such as nylon and polycarbonate. The desired material or materials forming sleeve 28 may establish a rigid structure with little or no malleability of sleeve 28, as in this embodiment of device 26. Instead, device 26 establishes a Modeling Configuration by including an inflatable lining 30 that may be selectively inflated by the caregiver or patient through tube 32 to expand inflatable lining 30, thereby applying with a selectively expanded inflatable lining 30 selective force against a curved portion of penis 10.

As shown in FIG. 4, inflatable lining 30 comprises a single inflatable region located on an interior surface of sleeve 28; however, multiple inflatable regions may alternatively be employed. Additionally, if multiple inflatable regions are employed, they may be employed simultaneously against one side of penis 10, or alternatively may be applied to multiple opposing sides of penis 10. Concerning the latter configuration of multiple inflatable regions applied to multiple opposing regions of penis 10, embodiments of the present invention may employ one inflatable region applying force in a first direction, and a second inflatable region applying force in an opposing direction, the two opposing forces tending to work together to straighten out and correct the shape of penis 10.

The interior surface of sleeve 28 may also have a coating of material or include an elastic fabric or elastomeric sheeting suitable for the patient's comfort. The coating material, elastic fabric or elastomeric sheeting (not shown) may reside on only the interior surface area of sleeve 28 (i.e., that portion in contact with penis 10). Exemplary coating materials including, without limitation Neoprene, Lycra, Spandex, silicone rubber, polyurethane, latex, vulcanized rubber, thermoplastic elastomers such as C Flex®, polypropylene, ePTFE, Teflon, non-woven, woven or knit fabrics composed of Lycra, cotton or the like or any other desired material providing some degree of coating compressibility to reduce patient discomfort from application of sleeve 28 against the penis 10.

In use, device 26 is placed over or wrapped around the patient's penis 10, as shown in FIG. 4. The caregiver or patient would then arrange device 26 such that it is positioned to apply a force from inflatable lining 30 (once expanded) against penis 10 that would tend to straighten out and correct the shape of penis 10. Once device 26 is in the desired position, the caregiver or patient would pump fluid (such as air) into inflatable lining 30 to apply the desired counteracting and correcting force to penis 10. Once the desired amount of modeling has taken place, the caregiver or patient would release the fluid from the inflatable lining 30, and remove the device 26 from the patient's penis 10. One embodiment of the pump or pressurization device (not shown) may resemble the hand-operated squeeze bulb attached to tube 32, similar to those utilized in concert with blood pressure cuffs (sphygmomanometers). In this embodiment, when pressurization is desired, the caregiver or patient hand actuates a release valve in fluid communication with the tube 32 (not shown), into a closed position, repeatedly squeezes the squeeze bulb to transfer fluid (such as air) into the inflatable lining, and repeats the squeezing process until a desired pressurization (and straightening of the penis) has occurred. In one embodiment, an overpressure safety valve in fluid communication with the tube 32 may be added to the squeeze bulb to prevent application of excessive pressure. In another embodiment, a pressure gauge is placed in fluid communication with the internal space of the inflatable lining 30, allowing the caregiver or patient to determine an amount of pressure currently being applied by pressurization. Once the desired treatment results (e.g. straightening or modeling) are obtained, the caregiver or patient may activate or open the release valve, allowing the fluid to escape, thereby causing deflation of the inflatable lining 30, which, in turn allows removal of device 26 from the patient's penis 10.

Figures 1, 5A:
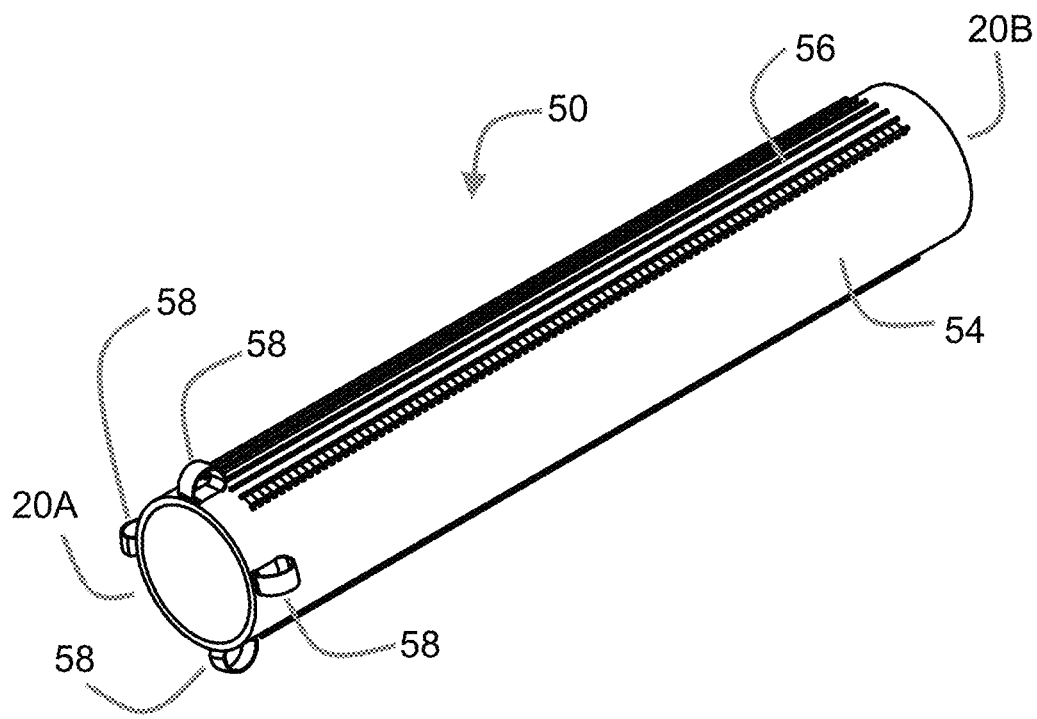
Figures 2, 5A:
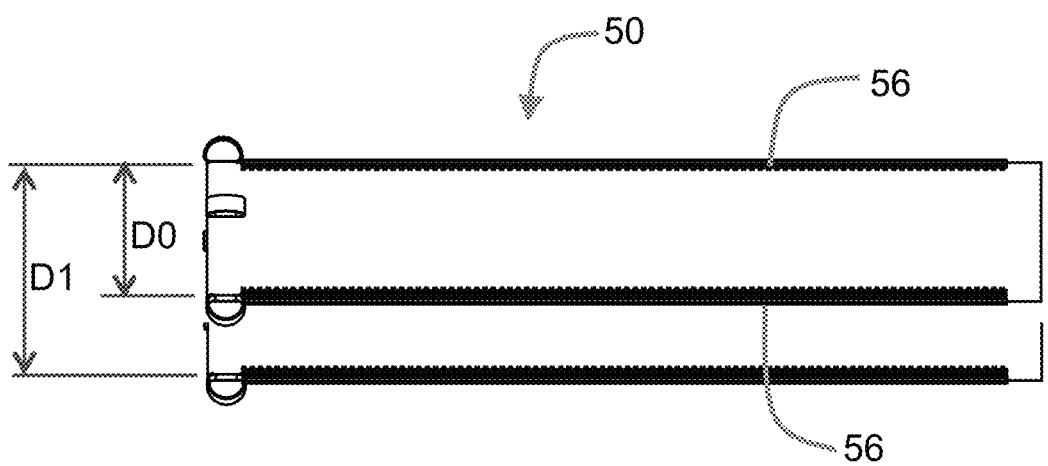
Figures 1, 5B:
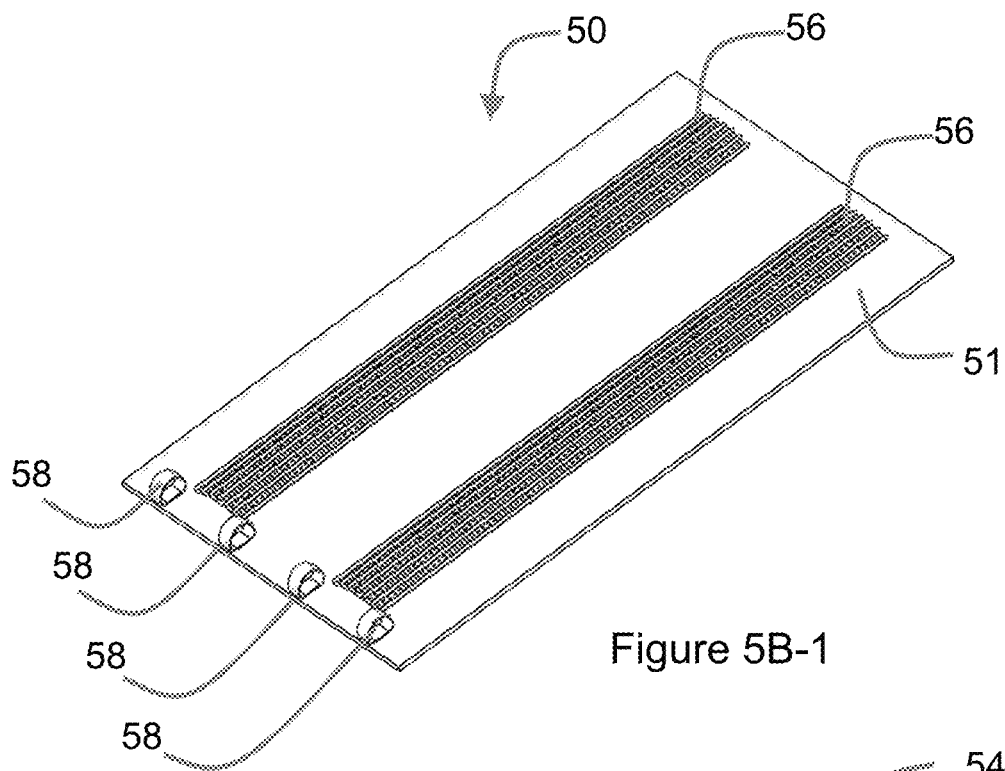
Figures 2, 5B:
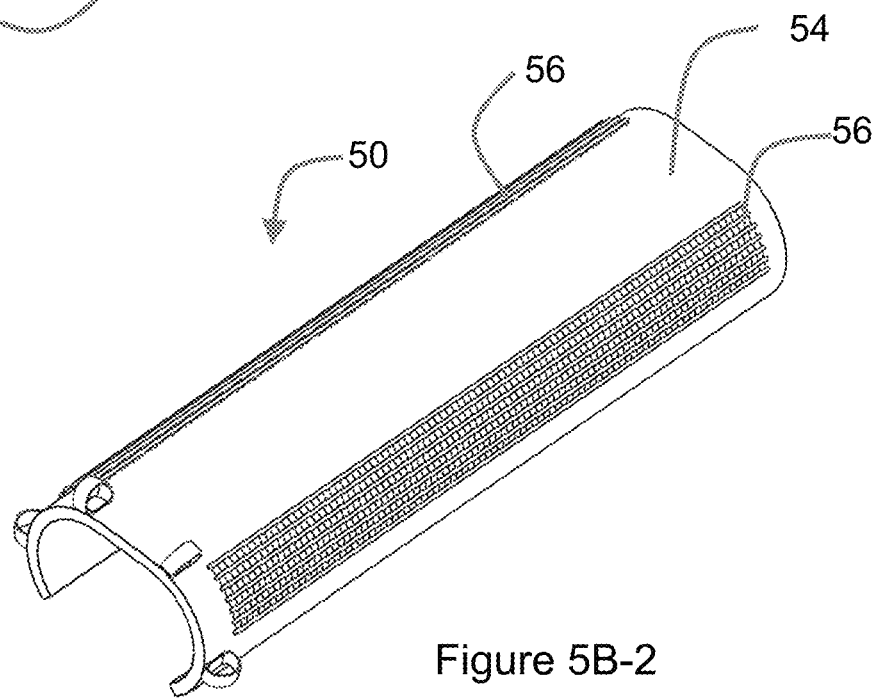

FIGS. 5A-1 through 5C-2 show a device 52 for penile modeling. Device 50, as shown, includes a generally cylindrical structure, assembly or sleeve 54 (although any other desired structural shape is permitted), including open ends 20A, 20B to facilitate insertion of device 50 over penis (not shown). The assembly 54 includes an elastic, resilient material which snugly and resiliently encircles the penis. The elastic material includes one or more regions which are reinforced with plastically deformable, i.e., malleable members 56. In FIGS. 5A-1, 5A-2, 5B-1 and 5B-2, two such malleable member 56 are provided; however, in practice any number of malleable members 56 including a single malleable member 56 may be used. In some examples, the malleable members 56 are evenly spaced around the circumference of the assembly or sleeve 54. In an example with two malleable members 56, the members are spaced 180 degrees apart. In an example with three malleable members 56, the members are spaced approximately 120 degrees apart. The malleable members may be covered with an elastic, resilient material (FIG. 5C-1).

In this embodiment of device 50, cylindrical sleeve 54 is formed from a sheet of resilient, elastic material which is reinforced with one or more sections of malleable (plastically deformable) material 56 such as steel mesh or the like. FIGS. 5A-1 and 5A-2 show device 50 with two discreet sections or regions of malleable material 56, however, in practice any number of sections may be used. The malleable material 56 may or may not span the entire circumference of the generally cylindrical sleeve 54. In FIGS. 5A-1 and 5A-2, the malleable material does not span the entire circumference of the cylindrical sleeve 54. Generally cylindrical sleeve (assembly) 54 may comprise a unitary cylindrical structure, as opposed to a generally cylindrical structure formed by structural members 21, 22 (e.g. as shown in FIGS. 1A, FIG. 2 and FIG. 3) and having related openings therebetween. Alternatively, cylindrical sleeve assembly 54 may be configured in a semi rolled flat sheet or flat sheet of material which is wrapped around the penis (FIGS. 5B-1and 5B-2 respectively) to form the cylindrical structure. In this example, there may be no need for a delivery device. The opposed edges of the sheet may be secured together using conventional closure mechanisms such as a hook-and-loop material (e.g., Velcro®), adhesive tape, clasps or the like (not shown). An opening or viewing port (not illustrated) may be formed or defined in the wall of the sleeve 54 such that the skin tone of the penis may be viewable without the need for removing the sleeve 54.

Device 50 may include one or more gripping portions 58 which may facilitate positioning or removal of the device 50. In FIGS. 5A-1 and 5A-2, the gripping portions 58 are depicted as loops which may be formed of a fabric material. The loops are not drawn to scale and may be smaller or larger in practice to enable and ease manual placement of the device on the penis by the caregiver or patient. FIGS. 5C-1 through 5C-3 depicts an example device 50 which includes finger-holes 58-1 instead of gripping portions 58 which may be used in addition to or instead of gripping portions 58. Finger-holes 58-1 may be reinforced, finger-sized holes or apertures. In use, the physician inserts his/her finger into one or more of the reinforced finger-hole(s) 58-1 to pull the device 50 off of the penis. Extended pieces of fabric, pull tabs or other common methods of gripping (not shown) may be used in addition to the loops and finger holes mentioned.

Moreover, the gripping portions 58 or finger-holes 58-1 may be provided on the proximal end of the device, the distal end of the device, and/or any location therebetween. Gripping portions 58, 58-1 may be provided on any of the embodiments described herein including the devices shown in FIGS. 1-4.

The elastic, resilient material or materials employed to form sleeve 54 may be selected from any desired material or materials, including, without limitation any combination of Neoprene, neoprene rubber bonded to Lycra®, Spandex®, polyester, polymeric or naturally occurring fabric, silicone rubber, polyurethane, latex, vulcanized rubber, thermoplastic elastomers such as C Flex®, polypropylene, ePTFE, Teflon, non-woven, woven or knit fabrics composed of Lycra, cotton or the like. The desired material or materials forming sleeve 54 may establish an elastic, stretchable structure having an initial diameter D0 which may be stretched into a larger delivery diameter D1 by a delivery device 60A, 60B, or 60C (shown and detailed in FIGS. 6A, 6B, and 6C-1). Once the device 50 and delivery device 60A, 60B, or 60C are delivered over the penis (not shown), the delivery device is carefully withdrawn while holding the device 50 in position over the penis, thereby allowing the sleeve 54 to retract to its relaxed (less stretched) diameter D0. Once device 50 is in place, the caregiver or patient uses a hand-applied force to mold the structure to establish a Modeling Configuration. In an alternate approach, during the Modeling Configuration, the surgeon, after installing penile implants, may cause an artificial erection by inflating penile implants, and adjust the shape of the device 50 to counter any undesired bends of the surgically-modified penis that become more apparent upon the artificial erection of the patient's penis. Alternatively, the surgeon may inflate the penile implants after insertion and shape adjustment of the device 50, and iterative inflations and adjustments to the shape of device 50 may be undertaken to achieve the desired straightening effects.

FIGS. 6A, 6B, and 6C-1 depict delivery devices 60A, 60B, and 60C which may be used to deliver the device 50 of FIG. 5. Delivery device 60A is a generally cylindrical device having a hollow interior 61 sized to fit over the penis. Delivery device 60A has a uniform diameter along the working length 63 of the device where the working length 63 extends at least the full length of the penis (not shown).

Delivery device 60B, 60C (FIGS. 6B and 6C-1) is/are similar to device 60A (FIG. 6A), but the proximal end 64-B is cone-shaped or frustoconical such that a diameter of the delivery devices 60B and 60C tapers from the proximal end 64-B. Delivery devices 60B and 60C are generally cylindrical device having a hollow interior 65 and 66, respectively, sized to fit over the penis. Delivery device 60B is shown with a continuous cone shape from proximal end 64-B to distal end 64-A. Delivery device 60C is shown with a short cone shape at portion of proximal end 64-B and transitions to the uniform diameter working length 63 of the delivery device 60C. This cone shape portion of the proximal end 64-B aids in loading of the device 50 to the delivery device 60C.

The distal end of the delivery devices 60A, and 60B may be provided with a grasping member 62 used to enable or ease manual positioning and/or removal of the device by the caregiver or patient.

Figure 6A:
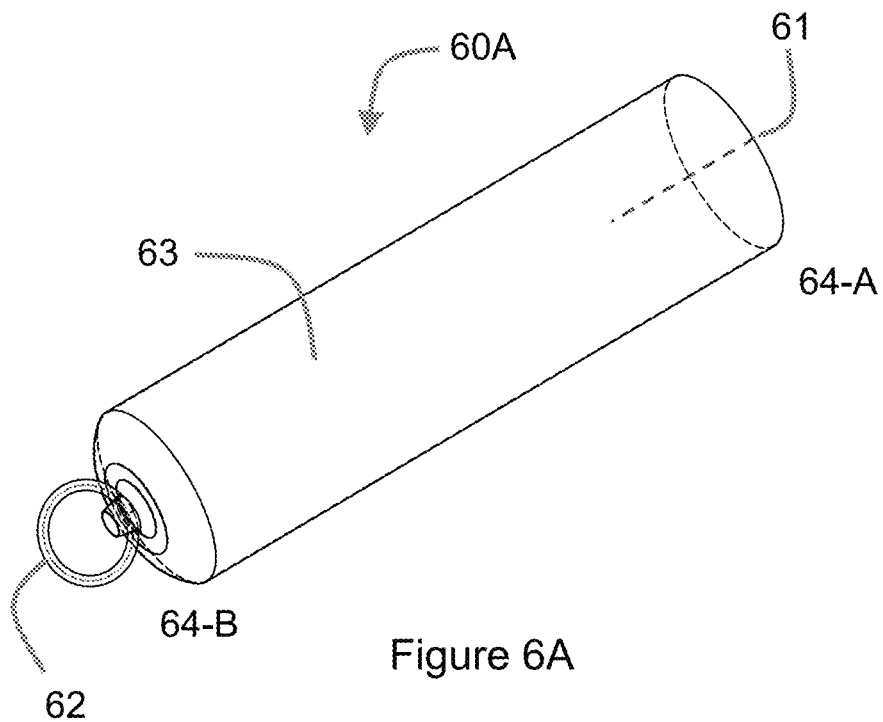
Figure 6B:
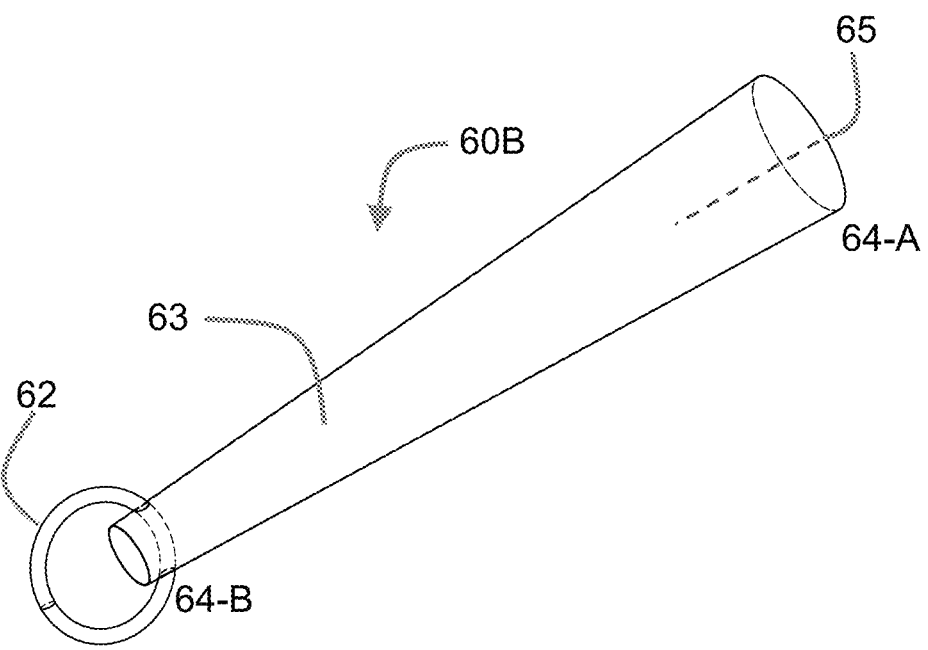
Figures 1, 6C:
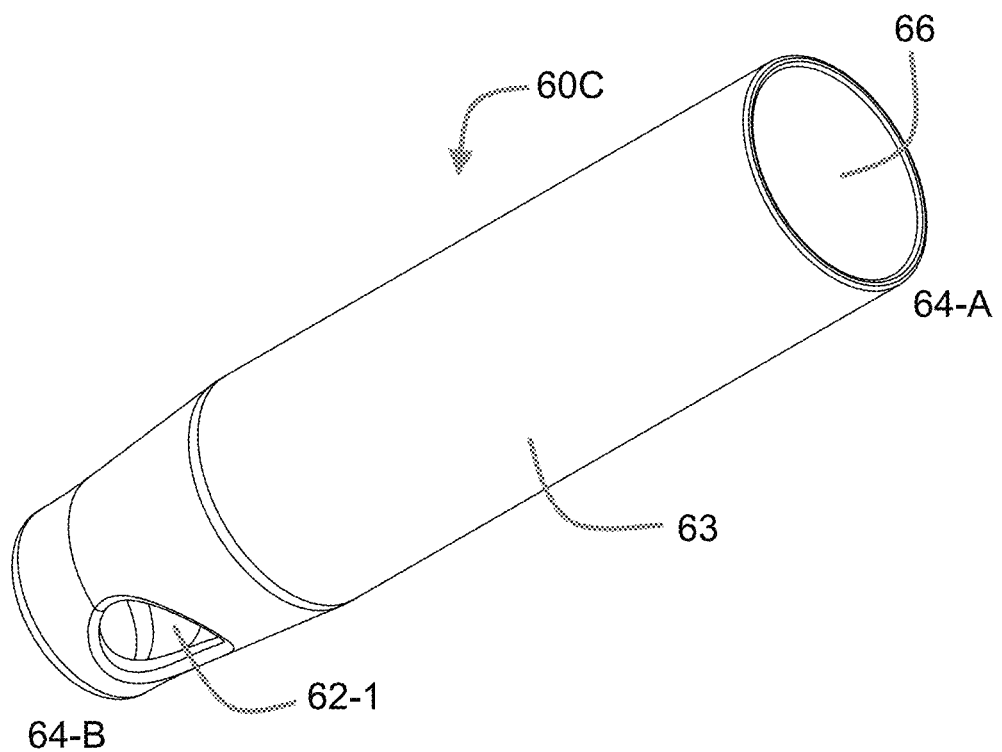
Figures 2, 6C:
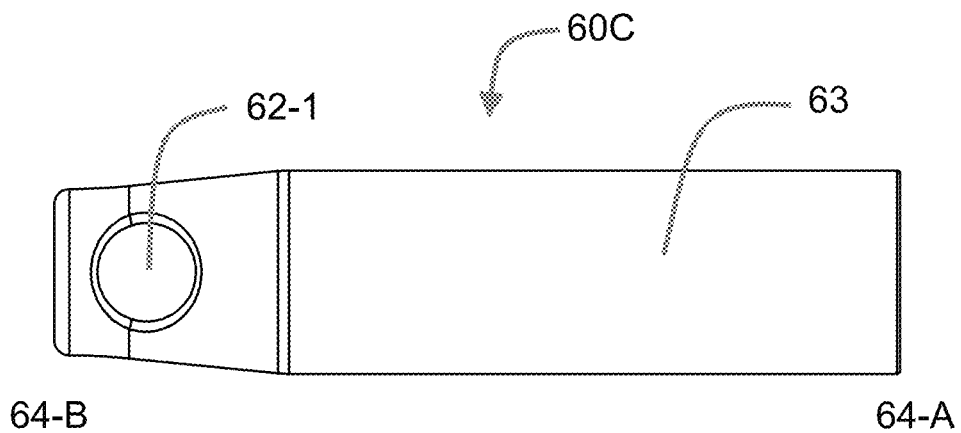
Figure 6D:
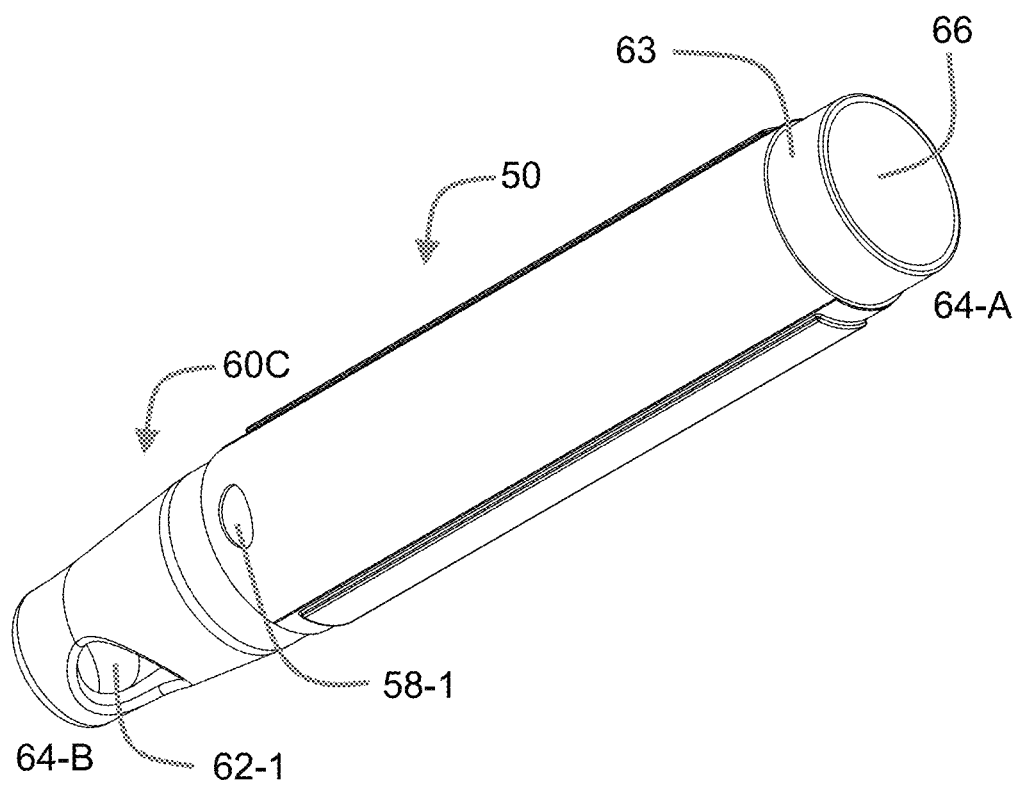
FIG. 6D shows a remodeling device mounted on a delivery tool.

In use the device 50 is coaxially mounted on the exterior surface of the delivery devices 60A, 60B, or 60C. To facilitate mounting the device 50 over the delivery device 60A, 60B, or 60C it may be desirable to form delivery device 60A, 60B, or 60C from a lubricious material, attach a lubricious material to the exterior circumference of delivery device, or to apply a lubricant to the exterior surface of the delivery device to facilitate the mounting of device 50 over the delivery tool. FIGS. 6C-1 and 6C-2 show delivery device 60C equipped with optional finger-holes 62-1 which may be used to facilitate delivery/removal of the delivery device. FIG. 6D shows remodeling device 50 coaxially mounted over delivery device 60C.

Figure 7:
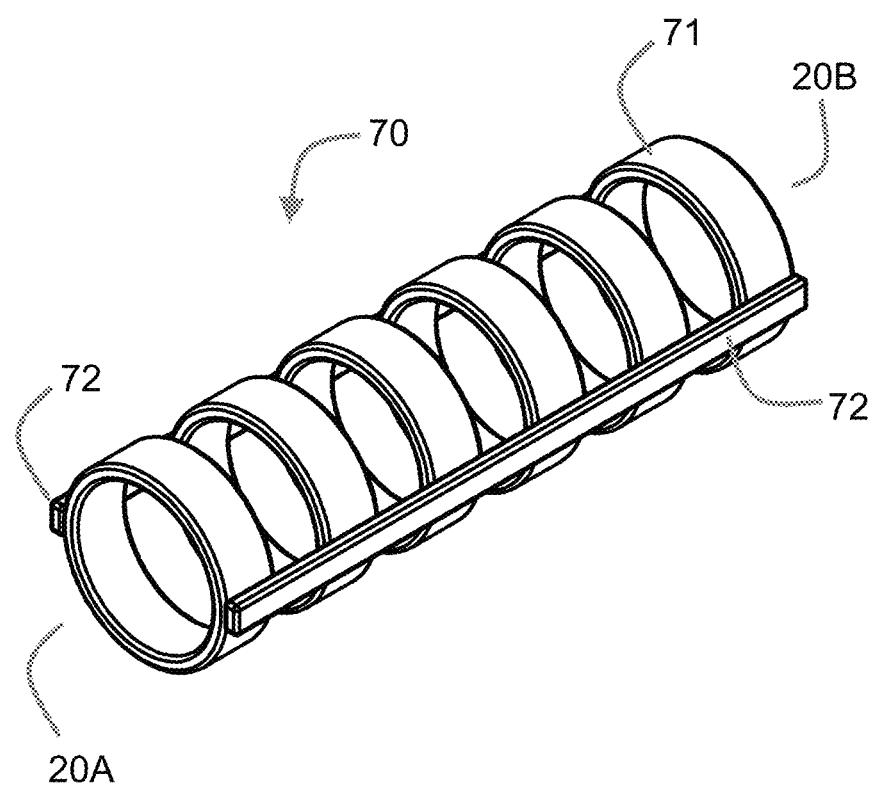
FIG. 7 is a fifth exemplary remodeling device.

FIG. 7 shows a device 70 for penile modeling. Device 70, as shown, includes a generally cylindrical structure (although any other desired structural shape is permitted), including open ends 20A, 20B to facilitate insertion of device 70 over penis (not shown). In this embodiment of device 70, an array of rings 71 and connecting members 72 create the structure of device 70. One or more connecting members 72 interconnect adjacent rings 71.

Rings 71 may be integrally formed as a closed loop, or alternatively ring 71 may be configured in a flat or semiround form (not shown) which is generally wrapped around the penis. The opposed edges of this alternative ring (not shown) may be secured together using conventional closure mechanisms such as a hook-and-loop material (e.g., Velcro®), adhesive tape, clasps or the like (not shown).

The material or materials employed to form the array of rings 71 and connecting members 72 of device 70 may be selected from any desired material or materials, including, without limitation, aluminum, steel, and non-hardened soft steel alloys, as well as plastic or polymer materials including polypropylene, nylon, polyethylene, polycarbonate, urethanes or the like. The desired material or materials forming the array of rings 71 and connecting members 72 of device 70 may establish a rigid structure with a level of malleability permitting a caregiver or patient to selectively bend and configure device 80 into a desired shape (i.e., bending device 80 into the Modeling Configuration).

According to one aspect, the rings 71 may be formed of a flexible material (metal, elastic, flexible fabric, silicone rubber, etc.) and the connecting members 72 are formed of a rigid yet malleable material.

According to another aspect, the rings 71 and the connecting members 72 are both formed of a rigid, yet malleable material.

Once device 70 is bent into the Modeling Configuration, device 70 retains sufficient structural rigidity to apply a counteracting force against a region of the penis (not shown) having the undesired curvature, without bending device 70 in a manner that reduces such counteracting force. In other words, the structural rigidity of device 70 is sufficient to prevent the region of undesired penile curvature from changing the shape of the Modeling Configuration.

The array of rings 71 and connecting members 72 of device 70 may also have a coating of material or include an elastic fabric or silicone sheeting suitable for the patient's comfort. The coating material, elastic fabric or silicone sheeting (not shown) may reside on only the interior surface area of device 70 (i.e., that portion in contact with penis (not shown)), or alternatively, may cover all exposed surfaces of the structural members 71, 72 forming device 70. Exemplary coating materials may include without limitation Neoprene, Lycra, Spandex, silicone rubber, polyurethane, latex, vulcanized rubber, thermoplastic elastomers such as C Flex®, polypropylene, ePTFE, Teflon, non-woven, woven or knit fabrics composed of Lycra, cotton or the like or any other desired material having some flexibility once applied to the array of rings 71 and connecting members 72 of device 70 and providing some degree of coating compressibility to reduce patient discomfort from application of device 70 in the Modeling Configuration against the penis (not shown).

In use, device 70 is inserted over or wrapped around the patient's penis. The caregiver or patient would then bend device 70 into a shape (i.e., again, the Modeling Configuration) in which a force would be applied against that portion of the penis (not shown) having undesired curvature, such that the applied force would tend to straighten out and correct the shape of penis (not shown). In an alternate approach, during the Modeling Configuration, the surgeon, after installing penile implants, may cause an artificial erection by inflating penile implants, and adjust the shape of the device 70 to counter any undesired bends of the surgically-modified penis that become more apparent upon the artificial erection of the patient's penis. Alternatively, the surgeon may inflate the penile implants after insertion and shape adjustment of the device 70, and iterative inflations and adjustments to the shape of device 70 may be undertaken to achieve the desired straightening effects.

In an exemplary method of use, the remodeling device may be:

(1) loaded over the outside surface of the delivery device 60A, 60B, or 60C (FIGS. 6A-6C1) if the remodeling device 50 (FIG. 5C-1) is not supplied preloaded. If supplied preloaded, then user may skip to step (2) of this exemplary method. The remodeling device is loaded onto the delivery device by placing an end of said remodeling device 50 over the delivery device as shown in FIG. 6D. While maintaining the delivery device in place, the remodeling device 50 is pulled and stretched over the stationary delivery device until the end of the remodeling device is positioned approximately flush with the end of the delivery device opposite of the grasping member.

(2) Place delivery device/remodeling device over the patient's erect, curved penis so that the devices cover part or all of the desired area of the penis which is to be remodeled. In some situations, the patient's penis may be catheterized prior to the remodeling of the penis. The delivery device/remodeling device are sized to fit over the widest portion of the catheter making it unnecessary to remove the catheter prior to placement of the delivery device/remodeling device over the patient's penis.

(3) While maintaining the remodeling device in position, by holding the gripping portions 58 or finger holes 58-1 (FIGS. 5A 5B, and 5C-1) of the remodeling device, retract the delivery device from within said remodeling device by pulling on the delivery device grasping members until it is completely disengaged from the remodeling device and penis. In some cases the user may wish to simply hold or grip the remodeling device around its perimeter to maintain the modeling device at a fixed position in relation to the patient's penis. Simultaneously grasp and pull and/or twist the delivery device distally from the patient until the delivery device 60A-60C (FIGS. 6A through 6C-1) is disengaged from the remodeling device. Removal of the delivery device allows the remodeling device to return to its generally relaxed position in apposition to the erect, curved penis.

(4) Surgeon, caregiver or patient may then bend the malleable portions of the remodeling device along with the erect penis within it from its curved configuration to a desired Modeling Configuration to help reshape said penis.

(5) Maintain the remodeling device in place in the Modeling Configuration for the desired period of time.

(6) Remove the remodeling device from the penis by pulling the end of the device or by using the gripping portions 58 or holes, 58-1 (FIG. 5) if such portions are included on the remodeling device being used.

An alternative embodiment of the method of use for the devices of the invention described herein includes the following steps:

(1) Place remodeling device 20, 25, 24, 70 (FIGS. 1, 2, 3 and 7 respectively) over the patient's erect, curved penis by wrapping the device around the shaft of the penis so that the remodeling device covers the area of the penis to be modeled.

(2) Surgeon, caregiver or patient may then bend the remodeling device along with the erect penis within it from its curved configuration to a desired Modeling Configuration to help reshape said penis.

(3) Maintain the remodeling device in place in the Modeling Configuration for the desired period of time.

(4) Remove the remodeling device from the penis by pulling the end of the device or by using the gripping portions 58, 58-1 (FIG. 5) if such portions are included on the remodeling device being used.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A device for remodeling a penis, comprising:
   a cylinder of resilient, elastic material which is reinforced with two or more discrete sections of plastically deformable material, at least one through-hole extending through a wall of said cylinder, said cylinder having a lumen extending between proximal and distal ends, the lumen sized to accommodate the penis when the cylinder is externally mounted over the penis the cylinder having an interior surface facing the lumen and an exterior surface facing away from the lumen, a longitudinal direction and a transverse direction, the transverse direction being orthogonal to the longitudinal direction, the discrete sections of plastically deformable material extend along a working length in a longitudinal direction and are circumferentially separated by sections of elastic material, the cylinder being adapted to snugly and resiliently grip the penis.

2. The device of claim 1, wherein the plastically deformable material is solid.

3. The device of claim 1, wherein the plastically deformable material is a mesh.

4. The device of claim 1, wherein the plastically deformable material is at least partially coated by a coating, covered by the elastic material, or embedded within the elastic material.

5. The remodeling device of claim 1, wherein the elastic material is selected from the group Neoprene, Lycra, Spandex, silicone rubber, polyurethane, latex, vulcanized rubber, thermoplastic elastomers, polypropylene, ePTFE, Teflon, non-woven fabrics, woven fabrics, and knit fabrics.

6. The remodeling device of claim 1, wherein the plastically deformable member is formed of a material selected from the group aluminum, steel, non-hardened soft steel alloys, plastic, polymeric materials, polypropylene, nylon, polyethylene, polycarbonate, and urethanes.

7. The remodeling device of claim 1, wherein the proximal and distal ends are atraumatic.

8. The remodeling device of claim 1, wherein the plastically deformable member is malleable at room temperature.

9. The remodeling device of claim 1, wherein the proximal and distal ends are covered with an atraumatic material.

10. The remodeling device of claim 1, further comprising at least one gripping portion provided on the exterior surface of the cylinder.

11. The remodeling device of claim 1, wherein the working length of the cylinder extends along a full length of the penis.

12. A device for remodeling a penis, comprising:
   a cylinder of resilient, elastic material which is reinforced with two or more discrete sections of plastically deformable material, said cylinder having a lumen extending between proximal and distal ends, the lumen sized to accommodate the penis when the cylinder is externally mounted over the penis the cylinder having an interior surface facing the lumen and an exterior surface facing away from the lumen, a longitudinal direction and a transverse direction, the transverse direction being orthogonal to the longitudinal direction, the discrete sections of plastically deformable material extend along a working length in a longitudinal direction and are circumferentially separated by sections of elastic material, the cylinder being adapted to snugly and resiliently grip the penis; and
   at least one inflatable lining provided on the interior surface, each one of the at least one inflatable lining being independently inflatable, thereby providing one or more inflatable regions.

13. A device for remodeling a penis, comprising:
   a cylinder of resilient, elastic material which is reinforced with two or more discrete sections of plastically deformable material, said cylinder having a lumen extending between proximal and distal ends, the lumen sized to accommodate the penis when the cylinder is externally mounted over the penis the cylinder having an interior surface facing the lumen and an exterior surface facing away from the lumen, a longitudinal direction and a transverse direction, the transverse direction being orthogonal to the longitudinal direction, the discrete sections of plastically deformable material extend along a working length in a longitudinal direction and are circumferentially separated by sections of elastic material, the cylinder being adapted to snugly and resiliently grip the penis; and
   at least one gripping portion provided on the exterior surface of the cylinder distal the distal end thereof;
   wherein when the cylinder is mounted over the penis, the distal end is positioned proximal the top of the penis;
   wherein the gripping portion is used to facilitate removal of the device from the penis;
   wherein the gripping portion is a loop of material.

* * * * *